US00PP17479P2

(12) United States Plant Patent
Bergman

(10) Patent No.: US PP17,479 P2
(45) Date of Patent: Mar. 6, 2007

(54) ***CHRYSANTHEMUM* PLANT NAMED 'SUNNY YOOLYMPIA'**

(50) Latin Name: *Chrysanthemum×morifolium*
Varietal Denomination: Sunny Yoolympia

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 30 days.

(21) Appl. No.: 11/157,409

(22) Filed: Jun. 21, 2005

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Sunny Yoolympia', characterized by its uniform and outwardly spreading plant habit; strong and freely branching growth habit; dark green-colored foliage; uniform flowering response and habit; typically grown as a disbud-type; early flowering habit; large decorative-type inflorescences with elongated oblong-shaped ray florets; light yellow-colored ray florets; and excellent postproduction longevity with plants maintaining good substance and color for about four to five weeks in an interior environment.

2 Drawing Sheets

Botanical designation: *Chrysanthemum×morifolium.*
Cultivar denomination: 'Sunny Yoolympia'.

BACKGROUND OF THE INVENTION

The present Invention relates to a new and distinct cultivar of *Chrysanthemum* plant, botanically known as *Chrysanthemum×morifolium* and hereinafter referred to by the name 'Sunny Yoolympia'.

The new *Chrysanthemum* is a product of a planned breeding program conducted by the Inventor in Alva, Fla. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* is a naturally-occurring whole plant mutation of the *Chrysanthemum×morifolium* cultivar Yoolympia, disclosed in U.S. Plant Pat. No. 14,814. The new *Chrysanthemum* was discovered and selected by the Inventor as a single flowering plant from within a population of plants of the cultivar Yoolympia in a controlled environment in Alva, Fla. on Dec. 1, 2002. The selection of this plant was based on its uniform plant growth habit, good vigor and strong branching habit, desirable inflorescence form and floret colors, fast and uniform flowering response, and good postproduction longevity.

Asexual reproduction of the new *Chrysanthemum* by vegetative tip cuttings was first conducted in Alva, Fla. in February, 2003. Asexual reproduction by cuttings has shown that the unique features of this new *Chrysanthemum* are stable and reproduced true to type in successive generations.

SUMMARY OF THE INVENTION

The cultivar Sunny Yoolympia has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Sunny Yoolympia'. These characteristics in combination distinguish 'Sunny Yoolympia' as a new and distinct *Chrysanthemum:*

1. Uniform and outwardly spreading plant habit.
2. Strong and freely branching growth habit.
3. Dark green-colored foliage.
4. Uniform flowering response and habit.
5. Typically grown as a disbud-type.
6. Early flowering 7.5 week response time.
7. Large decorative-type inflorescences with elongated oblong-shaped ray florets.
8. Light-yellow-colored ray florets.
9. Excellent postproduction longevity with plants maintaining good substance and color for about four to five weeks in an interior environment.

Plants of the new *Chrysanthemum* can be compared to plants of the parent, the cultivar Yoolympia. Plants of the new *Chrysanthemum* differ from plants of the cultivar Yoolympia primarily in ray floret coloration as plants of the cultivar Yoolympia have white-colored ray florets.

Plants of the new *Chrysanthemum* can be compared to plants of the cultivar Yomanhattan, disclosed in U.S. Plant Pat. No. 14,959. In side-by-side comparisons conducted in Alva, Fla., plants of the new *Chrysanthemum* differed from plants of the cultivar Yomanhattan in the following characteristics:

1. Plants of the new *Chrysanthemum* were larger and more vigorous than plants of the cultivar Yomanhattan.
2. Plants of the new *Chrysanthemum* flowered about three to four days earlier than plants of the cultivar Yomanhattan.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Sunny Yoolympia' grown as disbud-types.

The photograph on the second sheet comprises a close-up view of typical inflorescences of 'Sunny Yoolympia' grown as disbud-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif., in a fiberglass-covered greenhouse and under conditions which approximate those generally used in commercial potted *Chrysanthemum* production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about two weeks later. At the time of the pinch, the photoinductive short day/long night treatments were initiated. Plants used for the description were grown as disbud-types. Measurements and numerical values represent averages of typical flowering plants.

Botanical classification: *Chrysanthemum×morifolium* cultivar Sunny Yoolympia.

Commercial classification: Decorative-type potted *Chrysanthemum.*

Parentage: Naturally-occurring whole plant mutation of the *Chrysanthemum×morifolium* cultivar Yoolympia, disclosed in U.S. Plant Pat. No. 14,814.

Propagation:

*Type.*—Terminal tip cuttings.

*Time to initiate roots.*—About four days at 21° C.

*Time to produce a rooted cutting.*—About ten days at 21° C.

*Root description.*—Fibrous; white, close to 155D, in color.

*Rooting habit.*—Freely branching; moderately dense.

Plant description:

*Appearance.*—Herbaceous decorative-type potted *Chrysanthemum* that is typically grown as a disbud-type. Upright with lateral branches outwardly spreading; uniformly mounded crown. Strong and freely branching growth habit; about four lateral branches develop after removal of terminal apex (pinching); dense and full plants.

*Plant height.*—About 25.5 cm.

*Plant width.*—About 41 cm.

*Lateral branches (peduncles).*—Length: About 19 cm. Diameter: About 5 mm. Internode length: About 2.2 cm. Strength: Strong. Texture: Pubescent. Color: 146A.

*Foliage description.*—Arrangement: Alternate; simple. Length: About 9.75 cm. Width: About 6.8 cm. Apex: Acute. Base: Mostly truncate. Margin: Palmately lobed, sinuses between lateral lobes parallel to convergent. Texture, upper and lower surfaces: Pubescent. Color: Developing and fully expanded foliage, upper surface: Darker green to 147A. Developing and fully expanded foliage, lower surface: Close to 147A. Venation, upper surface: Close to 147A. Venation, lower surface: Close to 146A. Petiole length: About 2.7 cm. Petiole diameter: About 3 mm. Petiole texture, upper and lower surfaces: Pubescent. Petiole color, upper and lower surfaces: 146A.

Inflorescence description:

*Appearance.*—Decorative-type inflorescence form with elongated oblong-shaped ray florets. Inflorescences borne on terminals above foliage. Disk and ray florets develop acropetally on a capitulum. Inflorescences slightly fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to two weeks of long day/short night conditions followed by photoinductive short day/long night conditions flower about 7.5 weeks later.

*Postproduction longevity.*—Inflorescences maintain good color and substance for about four to five weeks in an interior environment.

*Quantity of inflorescences.*—Grown as a disbud-type, only one inflorescence is allowed to develop per lateral branch.

*Inflorescence bud.*—Height: About 5.5 mm. Diameter: About 6 mm. Shape: Oblate. Color: 144A to 146A.

*Inflorescence diameter.*—Large, about 9.5 cm.

*Inflorescence height.*—About 3.3 cm.

*Diameter of disc.*—About 4 mm; inconspicuous.

*Receptacle diameter.*—About 8 mm.

*Receptacle height.*—About 7 mm.

*Ray florets.*—Length: About 4.7 cm. Width: About 1 cm. Corolla tube length: About 6.5 mm. Shape: Elongate oblong. Apex: Acute to emarginate. Base: Fused into a corolla tube. Margin: Entire. Orientation: Initially upright to eventually reflexed. Texture, upper and lower surfaces: Smooth, glabrous; satiny. Number of ray florets per inflorescence: About 175 arranged in numerous whorls. Color: When opening and fully opened, upper surface: Close to 6C; color becoming closer to 6D to 5D with development. When opening and fully opened, lower surface: Close to 5D.

*Disc florets.*—Arrangement: Massed at center of receptacle. Length: About 4 mm. Diameter, apex: About 1 mm. Diameter, base: About 1 mm. Shape: Tubular; elongated. Apex: Five-pointed. Number of disc florets per inflorescence: About 18. Color: Immature: Close to 144A. Mature, apex: 9A. Mature, mid-section and base: Close to 155D.

*Phyllaries.*—Quantity per inflorescence: About 20 arranged in about two to three whorls. Length: About 1.1 cm. Width: About 6 mm. Shape: Lanceolate. Apex: Acute. Base: Truncate. Margin: Entire. Texture, upper surface: Waxy, smooth. Texture, lower surface: Pubescent. Color, upper surface: Close to 144A. Color, lower surface: 146A to 147A.

*Reproductive organs.*—Androecium: Present on disc florets only. Anther length: Less than 1 mm. Anther color: Close to 12A. Pollen amount: None observed. Gynoecium: Present on both ray and disc florets. Style length: About 6 mm. Style color: Close to 155D. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Sunny Yoolympia', as illustrated and described.

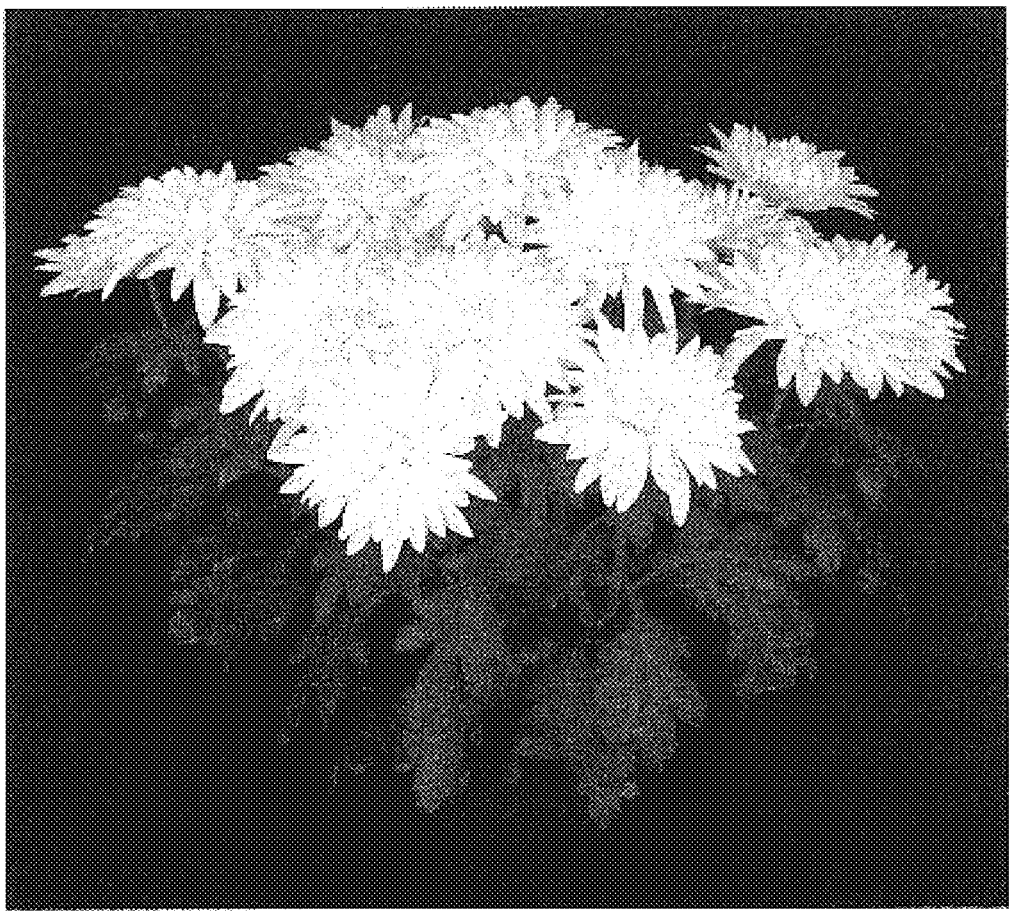

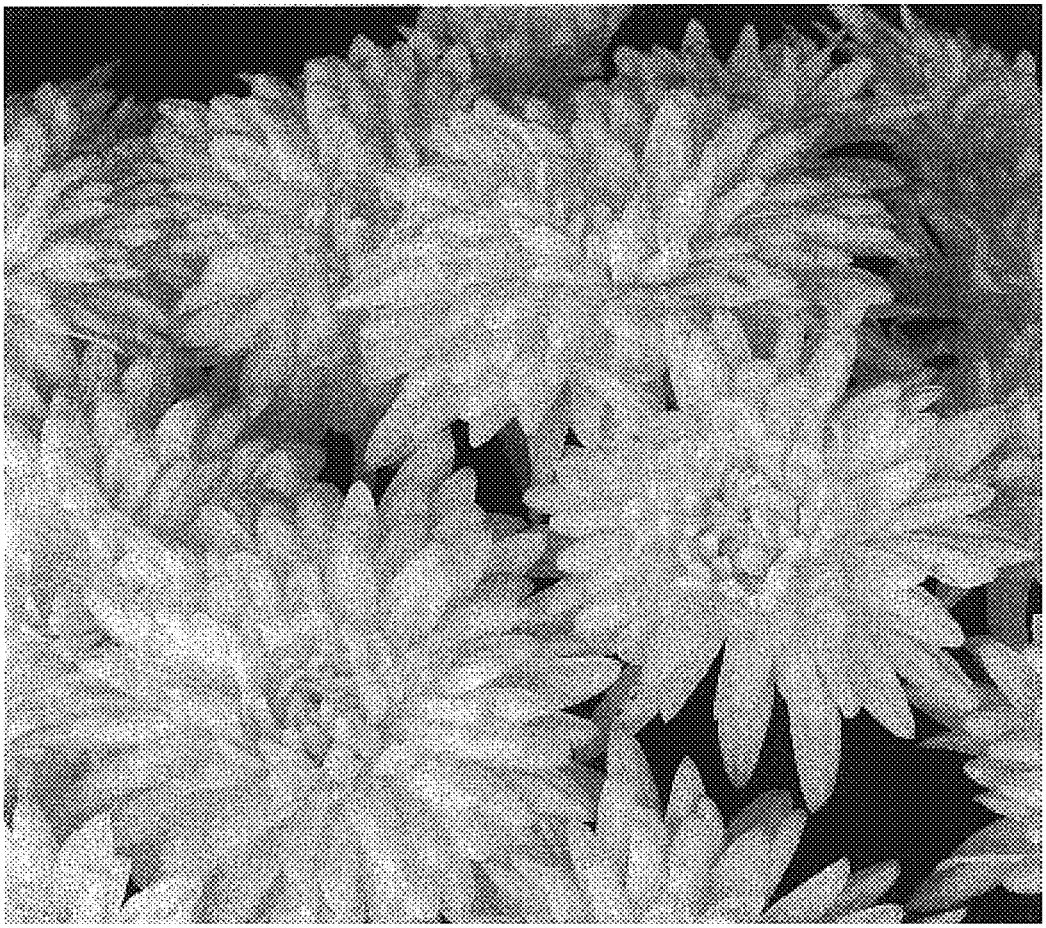

* * * * *